(12) United States Patent
Wilson

(10) Patent No.: US 10,111,850 B2
(45) Date of Patent: Oct. 30, 2018

(54) ESTER AND CHOLINESTERASE INHIBITOR IN LONG-ACTING NERVE BLOCK

(71) Applicant: Samuel Wilson, South Euclid, OH (US)

(72) Inventor: Samuel Wilson, South Euclid, OH (US)

( * ) Notice: Subject to any disclaimer, the term of this patent is extended or adjusted under 35 U.S.C. 154(b) by 0 days.

(21) Appl. No.: 14/956,066

(22) Filed: Dec. 1, 2015

(65) Prior Publication Data

US 2017/0151207 A1 Jun. 1, 2017

(51) Int. Cl.
| | | |
|---|---|---|
| *A61K 31/245* | (2006.01) | |
| *A61K 31/407* | (2006.01) | |
| *A61K 31/445* | (2006.01) | |
| *A61K 45/06* | (2006.01) | |

(52) U.S. Cl.
CPC .......... *A61K 31/245* (2013.01); *A61K 31/407* (2013.01); *A61K 31/445* (2013.01); *A61K 45/06* (2013.01); *H05K 999/99* (2013.01)

(58) Field of Classification Search
CPC ... A61K 31/245; A61K 31/407; A61K 31/445
See application file for complete search history.

(56) References Cited

U.S. PATENT DOCUMENTS 5,177,101 A * 1/1993 Glamkowski ........ C07D 487/04
514/411
5,912,271 A * 6/1999 Brodin ................. A61K 9/1274
424/489
6,395,291 B1 * 5/2002 Isacsson .............. A61K 31/445
424/400

OTHER PUBLICATIONS

J. Petersson et al., "A doube-blind trial of the analgesic properties of physostigmine in postoperative patients", Acta Anaesthesiol Scand. 1986, Abstract.
P.H. Tan et al., "Efficacy of Intrathecal Neostigmine for the Relief of Postinguinal Herniorrhaphy Pain", Acta Anaesthesiol Scand, 2000, vol. 44, pp. 1056-1060.
Ashraf S. Habib et al., "Use of Neostigmine in the Management of Acute Postoperative Pain and Labour Pain", CNS Drugs, Department of Anesthesiology, Duke University Medical Center, Durham, NC, 2006, vol. 20 No. 10, pp. 821-839.

* cited by examiner

*Primary Examiner* — Zohreh A Fay
(74) *Attorney, Agent, or Firm* — Crowell & Moring LLP

(57) ABSTRACT

Pharmaceutical compositions comprising an ester anesthetic and a cholinesterase inhibitor have been found to exhibit surprising and beneficial results in achieving a long-acting nerve block for example when administered to an interfascial plane or a peri-neural location in a subject. Such pharmaceutical compositions may also contain an amide anesthetic. Pharmaceutical compositions and methods of using such compositions as described herein provide a surprising and unexpected duration of pain control and a reduced need for the use of narcotics.

4 Claims, 3 Drawing Sheets

ESTER AND CHOLINESTERASE INHIBITOR IN LONG-ACTING NERVE BLOCK

BRIEF DESCRIPTION

Pharmaceutical compositions comprising an ester anesthetic and a cholinesterase inhibitor have been found to exhibit surprising and beneficial results in achieving a long-acting nerve block for example when administered to an interfascial plane or a peri-neural location in a subject. Such pharmaceutical compositions may also contain an amide anesthetic. Pharmaceutical compositions and methods of using such compositions as described herein provide a surprising and unexpected duration of pain control and a reduced need for the use of narcotics.

BACKGROUND OF THE INVENTION

Drug compositions that increase duration of pain control and decrease risk of tolerance and side effects are generally desirable. Due to side effects associated with narcotics, including for example sedation, respiratory depression, tolerance, and addiction, it is desirable to manage pain without narcotic drugs. However, non-narcotic methods of pain control are sometimes inadequate in intensity, duration or both.

For example, painkillers such as non-steroidal anti-inflammatory drugs (NSAIDs) are often not strong enough to control pain where a patient undergoes surgery or other invasive procedure or has suffered significant trauma. Although local anesthetics (e.g., amides) administered as nerve blocks can be useful for pain control, such blocks using amides are often inadequate in duration. Moreover, esters have not been an option of choice for use as a local anesthetic for nerve blocks, likely because the duration of pain control associated with ester drugs was known to be excessive, and to impair mobility for excessive durations, when esters were used as spinal anesthetics. Additionally, metabolism of esters by cholinesterases has potential for toxic effects by metabolites, such as 4-aminobenzoic acid (PABA).

As such, non-narcotic pharmaceutical compositions and corresponding methods of treatment that provide an adequate intensity and duration of pain management are desirable. The pharmaceutical compositions disclosed herein, which contain an ester anesthetic composition and a cholinesterase inhibitor compound, and methods of treatment using such pharmaceutical compositions unexpectedly provide advantages in management of pain. Optionally in a preferred embodiment, these pharmaceutical compositions may also contain an amide anesthetic.

Local anesthetic drug combinations and methods of treatment that can provide greater duration, reliability, reproducibility and a reduction in adverse events as compared with narcotics use (e.g., breathing difficulty, addiction) are highly desirable. The present pharmaceutical compositions and methods of treatment unexpectedly provide such advantages.

The present compositions and methods of treatment unexpectedly provide an increased duration of pain control by nerve block as compared with prior pharmaceutical compositions and methods for nerve block. As such, the present compositions and methods unexpectedly result in a decreased need for narcotic drug administration and provide decreased sedation and increased respiratory output as compared with prior pain control compositions and methods which employ narcotics. The present pharmaceutical compositions and methods of use provide unexpectedly high levels of patient satisfaction and decrease interventions required by health care personnel for pain management, including a beneficial effect on pain management particularly in the first 24 hour post-operative period.

SUMMARY OF THE INVENTION

The present invention includes and provides a pharmaceutical composition comprising an ester anesthetic or pharmaceutically acceptable salt thereof and a cholinesterase inhibitor or pharmaceutically acceptable salt thereof. For example, the present invention further includes and provides a pharmaceutical composition comprising about 10 mg to about 100 mg tetracaine or pharmaceutically acceptable salt thereof and about 100 μg to about 1000 μg physostigmine or pharmaceutically acceptable salt thereof. The present invention also includes and provides a pharmaceutical composition comprising about 10 mg to about 60 mg tetracaine or pharmaceutically acceptable salt thereof and about 100 μg to about 1000 μg physostigmine or pharmaceutically acceptable salt thereof.

The present invention includes and provides a pharmaceutical composition comprising about 10 mg to about 100 mg tetracaine or pharmaceutically acceptable salt thereof, about 100 μg to about 1000 μg physostigmine of pharmaceutically acceptable salt thereof, and about 0.1% to about 0.5% ropivacaine or pharmaceutically acceptable salt thereof. The present invention also includes and provides a pharmaceutical composition comprising about 10 mg to about 60 mg tetracaine or pharmaceutically acceptable salt thereof, about 100 μg to about 1000 μg physostigmine or pharmaceutically acceptable salt thereof, and about 0.1% to about 0.5% ropivacaine or pharmaceutically acceptable salt thereof.

The present invention includes and provides a pharmaceutical composition comprising about 10 mg to about 100 mg tetracaine or pharmaceutically acceptable salt thereof, about 100 μg to about 1000 μg physostigmine of pharmaceutically acceptable salt thereof, and about 0.35% to about 0.5% ropivacaine or pharmaceutically acceptable salt thereof. The present invention also includes and provides a pharmaceutical composition comprising about 10 mg to about 60 mg tetracaine or pharmaceutically acceptable salt thereof, about 100 μg to about 1000 μg physostigmine or pharmaceutically acceptable salt thereof, and about 0.35% to about 0.5% ropivacaine or pharmaceutically acceptable salt thereof.

The present invention further includes and provides a method of treating or preventing pain in a subject in need thereof, said method comprising administering a pharmaceutical composition comprising an ester anesthetic or pharmaceutically acceptable salt thereof and a cholinesterase inhibitor or pharmaceutically acceptable salt thereof to an interfascial plane or a peri-neural location in the subject. For example, the present invention includes and provides a method of treating or preventing pain in a subject in need thereof, said method comprising administering a pharmaceutical composition comprising about 10 mg to about 100 mg tetracaine or pharmaceutically acceptable salt thereof and about 100 μg to about 1000 μg physostigmine or pharmaceutically acceptable salt thereof to an interfascial plane or a peri-neural location in the subject. The present invention also includes and provides a method of treating or preventing pain in a subject in need thereof, said method comprising administering a pharmaceutical composition comprising about 10 mg to about 60 mg tetracaine or pharmaceutically acceptable salt thereof and about 100 μg to about 1000 μg physostigmine or pharmaceutically acceptable salt thereof to an interfascial plane or a peri-neural location in the subject.

The present invention also includes and provides a method of treating or preventing pain in a subject in need thereof, said method comprising administering a pharmaceutical composition comprising about 10 mg to about 100 mg tetracaine or pharmaceutically acceptable salt thereof, about 100 μg to about 1000 μg physostigmine or pharmaceutically acceptable salt thereof, and about 0.1% to about 0.5% ropivacaine or pharmaceutically acceptable salt thereof to an interfascial plane or peri-neural location in the subject. The present invention also includes and provides a method of treating or preventing pain in a subject in need thereof, said method comprising administering a pharmaceutical composition comprising about 10 mg to about 60 mg tetracaine or pharmaceutically acceptable salt thereof, about 100 μg to about 1000 μg physostigmine or pharmaceutically acceptable salt thereof, and about 0.1% to about 0.5% ropivacaine or pharmaceutically acceptable salt thereof to an interfascial plane or a peri-neural location in the subject.

The present invention also includes and provides a method of treating or preventing pain in a subject in need thereof, said method comprising administering a pharmaceutical composition comprising about 10 mg to about 100 mg tetracaine or pharmaceutically acceptable salt thereof, about 100 μg to about 1000 μg physostigmine or pharmaceutically acceptable salt thereof, and about 0.35% to about 0.5% ropivacaine or pharmaceutically acceptable salt thereof to an interfascial plane or a peri-neural location in the subject. The present invention also includes and provides a method of treating or preventing pain in a subject in need thereof, said method comprising administering a pharmaceutical composition comprising about 10 mg to about 60 mg tetracaine or pharmaceutically acceptable salt thereof, about 100 μg to about 1000 μg physostigmine or pharmaceutically acceptable salt thereof, and about 0.35% to about 0.5% ropivacaine or pharmaceutically acceptable salt thereof to an interfascial plane or a peri-neural location in the subject.

DETAILED DESCRIPTION OF THE INVENTION

Figure 1:
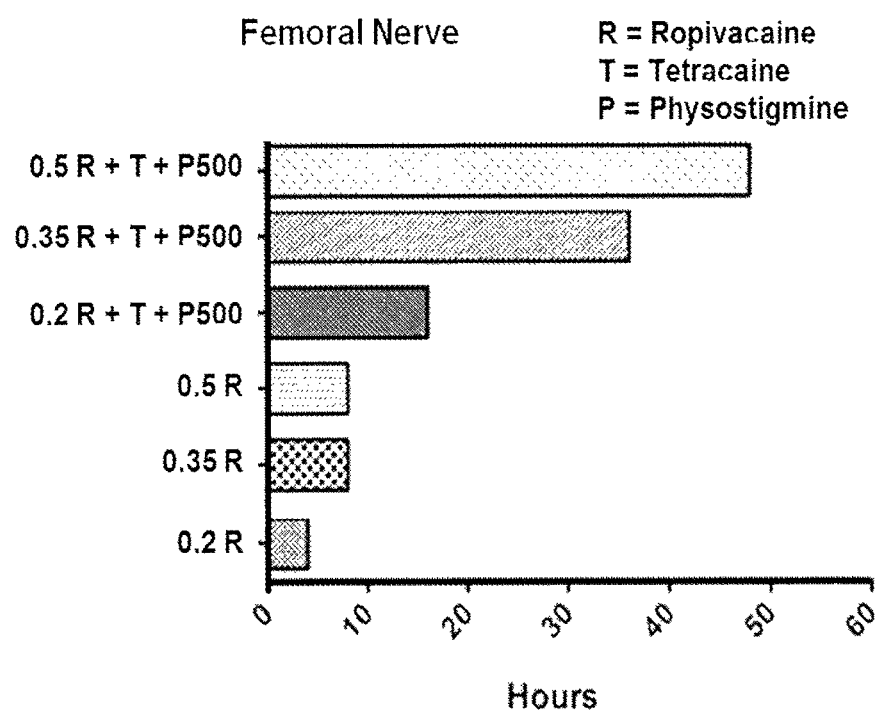
FIG. 1 shows femoral block duration in patients receiving 0.2%, 0.35% or 0.5% ropivacaine alone or 0.2%, 0.35%, or 0.5% ropivacaine with 40 mg tetracaine and 500 μg physostigmine.

By the present invention, a pharmaceutical composition comprising an ester anesthetic or pharmaceutically acceptable salt thereof and a cholinesterase inhibitor or physiologically acceptable salt thereof is provided. Such pharmaceutical compositions show surprising results and provide a longer than expected duration of pain control, particularly when administered as a nerve block to an interfascial plane or a peri-neural location in a subject.

Without being bound by theory, it is speculated that cholinesterase activity, effective to metabolize esters, is inhibited by the present pharmaceutical compositions and methods of use thereof, resulting in unexpectedly long action by the ester anesthetics. Without being limited, it is thought that surprising and unexpected pain control is achieved by the use of an ester anesthetic and cholinesterase inhibitor in a nerve block of an interfascial plane or peri-neural location because cholinesterases are found primarily in the bloodstream and because cholinesterase inhibitors further delay the breakdown of ester anesthetics.

In the context of the present invention, an ester anesthetic may include any ester anesthetic or pharmaceutically acceptable salt thereof, whether naturally-derived, wholly synthetic or partially synthetic. Non-limiting examples of ester anesthetics include benzocaine, chloroprocaine, cocaine, cyclomethylcaine, dimethocaine (larocaine), piperocaine, propoxycaine, procaine (novocaine), proparacaine and tetracaine (amethocaine) and pharmaceutically acceptable salts thereof. In an embodiment, an ester anesthetic is tetracaine.

Pharmaceutical compositions of the present invention may also include a cholinesterase inhibitor or pharmaceutically acceptable salt thereof. A cholinesterase inhibitor may be naturally-derived, wholly synthetic or partially synthetic. By way of example, a cholinesterase inhibitor is selected from the group consisting of pyridostigmine, physostigmine, donepezil, rivastigmine, galantamine, ambenonium, bethanechol, cevimeline, neostigmine, tacrine, and pharmaceutically acceptable salts thereof. In an embodiment, a cholinesterase inhibitor is pyridostigmine or physostigmine. In another embodiment, a cholinesterase inhibitor is physostigmine.

In a further embodiment, a pharmaceutical composition of the present invention may optionally comprise a carrier. In an embodiment, a carrier may be any pharmaceutically acceptable liquid used to provide an appropriate delivery volume for the desired route of delivery. By way of example, without limitation, a carrier may be selected from the group consisting of water, saline and an amide anesthetic or pharmaceutically acceptable salt thereof. In an embodiment, a carrier possibly may have anesthetic activity, but it is not necessary that a carrier have any anesthetic activity.

In an embodiment, a carrier is an amide anesthetic. Exemplary amide anesthetics include bupivacaine, ropivacaine, lidocaine, articaine, cinchocaine, etidocaine, levobupivacaine, mepivacaine, prilocaine, trimecaine and pharmaceutically acceptable salts thereof. In an embodiment, an amide anesthetic used as a carrier is ropivacaine.

In a pharmaceutical composition of the present invention, it is envisioned that a pharmaceutically acceptable salt may optionally be substituted for an ester anesthetic, cholinesterase inhibitor or amide anesthetic. Generally, as used herein, a pharmaceutically acceptable salt refers to a compound prepared by the reaction of an organic acid or base drug with a pharmaceutically acceptable mineral or organic acid or base. As used herein, a pharmaceutically acceptable salt may include hydrates and solvates of salts made in accordance with this invention. Exemplary pharmaceutically acceptable mineral or organic acids or bases are as listed for example in Tables 1-8 in *Handbook of Pharmaceutical Salts*, P. H. Stahl and C. G. Wermuth (eds.), VHCA, Zurich, pp. 334-345 (2002).

Examples of pharmaceutically acceptable salts include without limitation salts of hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and aspartic acid. In a preferred embodiment, a pharmaceutically acceptable salt is the hydrochloride salt.

Dosages of ester anesthetic and cholinesterase inhibitor in a pharmaceutical composition of the present invention will vary based on a number of factors, including for example patient pain level, pain type, pain tolerance, source of pain, age, height, weight, route of administration, and desired duration of effect.

The dosage of an ester anesthetic, such as for example tetracaine, that is administered as a nerve block to an interfascial plane or peri-neural location may vary for example without limitation from about 10 mg/block to about 100 mg/block.

The dosage of an ester anesthetic in a nerve block to an interfascial plane or peri-neural location may be for example in the range of about 10 mg/block to about 80 mg/block, about 10 mg/block to about 60 mg/block, about 10 mg/block to about 40 mg/block, about 20 mg/block to about 100 mg/block, about 40 mg/block to about 100 mg/block, about 60 mg/block to about 100 mg/block, about 80 mg/block to about 100 mg/block, about 20 mg/block to about 80 mg/block, or about 40 mg/block to about 60 mg/block.

The dosage of an ester anesthetic in a nerve block to an interfascial plane or peri-neural location may be for example about 10 mg/block, about 20 mg/block, about 30 mg/block, about 40 mg/block, about 50 mg/block, about 60 mg/block, about 70 mg/block, about 80 mg/block, about 90 mg/block, or about 100 mg/block.

The dosage of a cholinesterase inhibitor, such as physostigmine, that is administered as a nerve block to an interfascial plane or peri-neural location may vary by way of non-limiting example from about 100 µg/block to about 1000 µg/block.

By way of example, the dosage of cholinesterase inhibitor in a nerve block to an interfascial plane or pen-neural location may be in the range of about 200 µg/block to about 1000 µg/block, about 300 µg/block to about 1000 µg/block, about 400 µg/block to about 1000 µg/block, about 500 µg/block to about 1000 µg/block, about 600 µg/block to about 1000 µg/block, about 700 µg/block to about 1000 µg/block, about 800 µg/block to about 1000 µg/block, about 900 µg/block to about 1000 µg/block, about 100 µg/block to about 200 µg/block, about 100 µg/block to about 300 µg/block, about 100 µg/block to about 400 µg/block, about 100 µg/block to about 500 µg/block, about 100 µg/block to about 600 µg/block, about 100 µg/block to about 700 µg/block, about 100 µg/block to about 800 µg/block, about 100 µg/block to about 900 µg/block, about 200 µg/block to about 800 µg/block, about 300 µg/block to about 700 µg/block, about 400 µg/block to about 600 µg/block.

By way of example, the dosage of a cholinesterase inhibitor in a nerve block may be about 100 µg, about 200 µg, about 300 µg, about 400 µg, about 500 µg, about 600 µg, about 700 µg, about 800 µg, about 900 µg, or about 1000 µg.

Dosages as provided herein refer to dosages of active ingredient. These dosages may be varied, e.g., increased, where a pharmaceutical composition is delivered to the bloodstream, cerebrospinal fluid (CSF) or another location where cholinesterases are present. Pharmaceutically active ingredients should be added in the smallest dose of active ingredient to achieve satisfactory pain therapy or other desired pharmacological effect. To the extent possible, pharmaceutically active ingredients should be administered to maximize therapeutic effect without the occurrence of intolerable side effects.

The dosage of ester anesthetic generally will be increased where administration is to an area other than an avascular plane. An avascular plane is one that is not highly vascularized. In other words, the higher the blood supply in an area to which an ester drug is administered, the higher the dosage of ester anesthetic generally must be. Upper tolerance levels for ester drugs and concerns regarding metabolites and toxic products will be understood by the skilled artisan in light of the literature.

The dosage of ester anesthetic generally will be increased where administration is to an area other than an interfascial plane or peri-neural location. Where administration is to a more vascular area (e.g., not an interfascial plane or peri-neural location) such as intravenous, skin, muscle, or other soft tissue, the dosage of ester anesthetic may be increased to between about 2× and about 50×, between about 10× and about 25×, between about 25× and about 50×, between about 2× and about 10×, or between about 2× and about 5×, including for example about 2×, about 3×, about 4× or about 5× the dosage used for administration to an interfascial plane or a peri-neural location.

The dosage of ester anesthetic and cholinesterase inhibitor generally will be increased where administration is to an area other than an avascular plane. The dosage of cholinesterase inhibitor generally will be increased where administration is to an area other than an interfascial plane or a peri-neural location. Where administration is to a more vascular area (e.g., not an interfascial plane or a peri-neural location) such as intravenous, skin, muscle, or other soft tissue, the dosage of cholinesterase inhibitor may be increased about 2× to about 10×, for example about 2×, about 3×, about 4×, about 5×, about 6× about 7×, about 8×, about 9× or about 10×. In a preferred embodiment, the cholinesterase inhibitor is less than 2000 µg.

One or more carriers may also be included in order to provide a suitable medium for administration. In an embodiment, a carrier may be selected from the group consisting of water, saline and an amide anesthetic or pharmaceutically acceptable salt thereof. In an embodiment, a carrier may be an amide anesthetic.

Amide anesthetics include any amide anesthetic known to the skilled artisan such as, for example without limitation, bupivacaine, ropivacaine, lidocaine, articaine, cinchocaine, etidocaine, levobupivacaine, mepivacaine, prilocaine, trimecaine, or pharmaceutically acceptable salts thereof. In an embodiment, a pharmaceutical composition of the present invention comprises a ropivacaine solution as a carrier.

A carrier may be provided in any concentration appropriate to facilitate administration in accordance with methods of the present invention. For liquid delivery forms, the percentage of carrier solution is measured as mg carrier per mL total solution, i.e., as used herein, liquid carriers are measured as weight of carrier per unit volume to be delivered, expressed as a percent. For solid or semi-solid delivery forms, percentage of carrier is measured as a weight/weight percent, i.e., mg carrier per mg of drug form to be delivered.

In an embodiment, a carrier is a liquid solution of ropivacaine from about 0.1% to about 0.5% ropivacaine. In another embodiment, a carrier is a ropivacaine solution of about 0.2% to about 0.4%. In other embodiments, a carrier is a ropivacaine solution of about 0.1%, about 0.2%, about 0.25%, about 0.3%, about 0.35%, about 0.4%, about 0.45%, or about 0.5%.

As will be appreciated by the skilled artisan, dosage of a carrier, including an amide anesthetic may remain in the ranges as indicated, or may be varied or omitted to provide a suitable medium for administration.

A pharmaceutical composition of the present invention may be formulated with one or more pharmaceutically acceptable ingredients such as excipients. Any excipients known to the skilled artisan may be used in the pharmaceutical compositions of the present invention as will be appreciated by the skilled artisan. The following excipients are merely exemplary and may be substituted by other excipients known to the skilled art worker. Further exemplary excipients may be found for example in the Handbook of Pharmaceutical Excipients, (Raymond C. Rowe et al., eds.), 5$^{th}$ edit, APhA, London (2006).

A non-limiting example of excipients includes anti-adherents such as for example magnesium stearate to reduce adhesion or prevent sticking or both, binders such as for example saccharides and their derivatives (e.g., disaccharides such as sucrose and lactose, polysaccharides and their derivatives such as starches, cellulose, modified cellulose including for example microcrystalline cellulose and cellulose ethers such as for example hydroxylpropyl cellulose (HPC)), sugar alcohols (e.g., xylitol, sorbitol, maltitol), protein (e.g., gelatin), and synthetic polymers (e.g., polyvinylpyrrolidone (PVP) and polyethylene glycol (PEG)).

Another non-limiting example of excipients that may be included in the compositions of the present invention includes coatings such as for example cellulose (e.g., hydroxyproply methylcellulose (HPMC), synthetic polymers, shellac, corn protein zein or other polysaccharides), gelatin, fatty acids, waxes shellac, plastics and plant fibers. A coating may be used in a tablet, capsule. Tablets may also be uncoated. A coating may be enteric or non-enteric.

Other non-limiting excipients that may be included in the compositions of the present invention are colorings (e.g., titanium oxide and azo dyes), disintegrants (e.g., crosslinked polymers such as crosslinked polyvinylpyrrolidone, crosslinked sodium carboxymethyl cellulose, modified starch such as sodium starch glycolate, gelatin or acacia), flavorings (e.g., fruit extracts or artificial flavorings), glidants (e.g., fumed silica, talc, or magnesium carbonate), lubricants (e.g., talc, silica, fats such as vegetable stearin, magnesium stearate or stearic acid), preservatives (e.g., antioxidants such as vitamin A, vitamin E, vitamin C, retinyl palmitate, or selenium, amino acids such as cysteine or methionine, citric acid, sodium citrate, or synthetic preservatives such as methyl paraben or propyl paraben), sorbents (e.g., dessicants), sweeteners (e.g., sugar), or vehicles (e.g., petroleum or mineral oil).

In some instances, another active ingredient may be co-administered with a pharmaceutical composition of the present invention. Co-administration includes simultaneous administration (either together in the same dosage form or separately) or sequential administration.

Another active ingredient may allow an ester anesthetic or cholinesterase inhibitor to be administered in a lesser amount than in the absence of the other ingredient or vice versa. For example, the dosage of the other pharmaceutically active ingredient may be lowered while still achieving satisfactory pain therapy or other desired pharmacological effect. Alternatively or additionally, the dosage of the ingredients in a pharmaceutical composition of the invention may be lowered while still achieving satisfactory pain therapy when another ingredient is co-administered with a pharmaceutical composition of the present invention.

Other ingredients that may be added to a pharmaceutical composition of the present invention include without limitation, propranolol, ketamine, corticosteroids (e.g., cortisol, cortisone, prednisone, prednisolone, dexamethasone, betamethasone, triamcinolone, beclometasone, fludrocortisone, deoxycorticosterone acetate, or aldosterone), α- and β-adrenergic agonists (e.g., clonidine, decadron, epinephrine), vasoconstrictors (e.g., phenylephedrine, stimulants, antihistamines such as diphenhydramine), or botulinum toxin. It is envisioned that such ingredients may be administered simultaneously (either together or separately) or sequentially.

In addition to an ester anesthetic and a cholinesterase inhibitor, pharmaceutical compositions of the present invention may further comprise other pharmaceutically active ingredients such as for example, opioids, non-opioid analgesics, skeletal muscle relaxants, non-barbituate sedatives, and other such pharmaceutically active components, which may be administered simultaneously (either together or separately) or sequentially.

In general, other pharmaceutically active ingredients may be administered in amounts up to their maximum daily dose for the applicable procedure, which is known to those skilled in the art. Indeed, recommended doses of these other ingredients are well known to the skilled artisan and may be found in the literature, including for example in the Physician's Desk Reference, PDR Network, 68$^{th}$ edition (2014).

The amount of another pharmaceutically active ingredient will preferably be an amount that is equieffective to its activity in the absence of an ester anesthetic and a cholinesterase inhibitor. In this regard, "equieffective" refers to the dosage of the other pharmaceutically active ingredient that would be required in order to achieve the equivalent desired therapeutic effect as when the other ingredient is administered alone. This lesser amount can be calculated by the skilled artisan based on measurement of $ED_{50}$ values of the other pharmaceutically active ingredient with and without co-administration of an ester anesthetic and a cholinesterase inhibitor according to the present invention.

Interaction studies may be performed in order to determine the requisite dosage of the other pharmaceutically active ingredient by comparing the theoretically additive effect of a defined dosage of the other pharmaceutically active ingredient with the experimentally determined effect of the other pharmaceutically active ingredient when combined with a pharmaceutical composition comprising an ester anesthetic and a cholinesterase inhibitor of the present invention. Efficacy calculation should be measured at the time point of peak effect of the other pharmaceutically active ingredient.

In the context of the present invention, a pharmacologically effective amount refers to an amount of drug used to produce a desired pharmacological effect in a subject. A pharmacologically effective amount may be anticipated on the basis of in vitro testing or clinical testing. A pharmacologically effective amount may also be discerned based on the experience and judgment of a clinician.

A pharmaceutical composition of the present invention may be administered in any form known to the skilled artisan. See e.g., Remington: The Science and Practice of Pharmacy, 19$^{th}$ edition, Mack Pub. Co., Easton, Pa. (1995). A pharmaceutical composition of the present invention may be formulated for administration that is oral (including immediate release, extended release, and continuous release forms); nasal; ophthalmic; transdermal; parenteral (for example, intravenous, intramuscular, subcutaneous, intraventricular, intrathecal, spinal, epidural, intracerebroventricular); transcutaneous, sublingual, or transbuccal injection. A pharmaceutical composition of the present invention may be administered by means of a transdermal device such as a patch. A pharmaceutical composition of the present invention may be administered by a permanent catheter. Any other means of delivery known to the skilled artisan may be used, it being specifically understood that the foregoing list is not all inclusive.

An extended release formulation may include the use of liposomes, hydrophobic based polymer particles such as poly(lactic-co-glycolic acid) microspheres, pasty injectable and solid polymers like poly(sebacic-co-ricinoleic acid) as described for example in Weiniger, *Anaesthesia*, 67: 906-916 (2012).

In an embodiment, a pharmaceutical composition of the present invention can be formulated as a liquid (including an injectable solution, injectable suspension, nebulized solution, nebulized suspension, or oral liquid), powder, or elixir. Formulations for oral use can be provided as tablets, caplets or hard capsules wherein the pharmacologically active ingredients are mixed with an inert solid diluent such as calcium carbonate, sodium carbonate, calcium phosphate, lactose, talc, or kaolin, or as soft gelatin capsules wherein the active ingredients are mixed with an oleaginous medium, e.g., liquid paraffin or olive oil. Inert diluents and carriers which may be used in capsules include, for example, calcium carbonate, calcium phosphate, and kaolin.

A pharmaceutical composition of the present invention may be formulated for topical use for example in the form of a salve, rub, cream, topical ointment, gel, patch, or ophthalmic preparation.

In a preferred embodiment, a pharmaceutical composition of the present invention is formulated as a liquid solution for delivery to an avascular plane in a subject. In a preferred embodiment, a pharmaceutical composition of the present invention is formulated as a liquid solution, suspension or emulsion for delivery as a nerve block to an interfascial plane or a peri-neural location in a subject.

The present invention includes methods for treating or preventing pain in a subject in need thereof, comprising administering a pharmaceutical composition of the present invention, wherein pain is reduced or eliminated. For example, the present invention includes methods of treating or preventing pain in a subject in need thereof comprising an ester anesthetic or pharmaceutically acceptable salt thereof and a cholinesterase inhibitor or pharmaceutically acceptable salt thereof to a subject. Any ester anesthetic and cholinesterase inhibitor known to the skilled artisan may be used, including various examples of each of which are provided herein. In further embodiments, any one or more of water, saline and an amide anesthetic or pharmaceutically acceptable salt thereof may be added as a carrier.

By way of non-limiting example, the present invention includes a method of treating or preventing pain in a subject in need thereof, said method comprising administering a pharmaceutical composition comprising an ester anesthetic or pharmaceutically acceptable salt thereof and a cholinesterase inhibitor to an interfascial plane or a peri-neural location in the subject. For example, the present invention includes a method of treating or preventing pain in a subject in need thereof, said method comprising administering a pharmaceutical composition comprising about 10 mg to about 100 mg tetracaine or pharmaceutically acceptable salt thereof and about 100 µg to about 1000 µg physostigmine or pharmaceutically acceptable salt thereof to an interfascial plane or peri-neural location in the subject.

In a further embodiment, the present invention includes a method of treating or preventing pain in a subject in need thereof, said method comprising administering a pharmaceutical composition comprising an ester anesthetic or pharmaceutically acceptable salt thereof, a cholinesterase inhibitor or pharmaceutically acceptable salt thereof, and a carrier selected from the group consisting of water, saline and an amide anesthetic or pharmaceutically acceptable salt thereof to an interfascial plane or a peri-neural location in the subject. In an embodiment, the method of treating or preventing pain comprises administering a pharmaceutical composition comprising an ester anesthetic or pharmaceutically acceptable salt thereof, a cholinesterase inhibitor or pharmaceutically acceptable salt thereof, and an amide anesthetic carrier to an interfascial plane or a peri-neural location in the subject.

For example, the present invention includes a method of treating or preventing pain in a subject in need thereof, said method comprising administering a pharmaceutical composition comprising about 10 mg to about 100 mg tetracaine or pharmaceutically acceptable salt thereof, about 100 µg to about 1000 µg physostigmine or pharmaceutically acceptable salt thereof, and about 0.1% to about 0.5% ropivacaine or pharmaceutically acceptable salt thereof to an interfascial plane or a peri-neural location in the subject.

Pharmaceutical compositions may be administered by way of direct application to any body tissue, including for example adipose (i.e., fatty) tissue, dermal layers, or muscle. Administration may be, for example without limitation, oral, nasal, ophthalmic, transdermal, parenteral (for example, intravenous, intramuscular, subcutaneous, intraventricular, intrathecal, spinal, epidural, intracerebroventricular), transcutaneous, sublingual, and transbuccal injection.

One preferred route of administration for a pharmaceutical composition of the present invention is via nerve block to a peri-neural location. The skilled artisan will understand the meaning of a peri-neural location. As understood in the art, a peri-neural location in a subject is an area around a nerve. A peri-neural location is an area in proximity to a nerve. A peri-neural location is an area to which local anesthetic may be delivered in the form of a pain block.

Another preferred route of administration for a pharmaceutical composition of the present invention is via nerve block to an interfascial plane. The skilled artisan will understand the meaning and location of an interfascial plane. As understood in the art, an interfascial plane in a subject is an area between tissues that are enclosed, separated, or both enclosed and separated. An interfascial plane occurs at a location where tissue changes direction, angle, functional movement, or some combination thereof. An interfascial plane may be found, for example, between groups of muscles, between groups of nerve bundles, or between groups of connective tissue (e.g., as in joint spaces).

Exemplary, non-limiting interfascial nerve blocks in accordance with the present invention include trans-abdominal plane (TAP) block, sciatic nerve block, femoral nerve block, popliteal nerve block, iliac nerve block, inguinal nerve block, ilioinguinal nerve block, digital nerve block, trigeminal nerve block, ophthalmic nerve block, supraorbital nerve block, maxillary nerve block, sphenopalatine nerve block, cervical plexus nerve block, cervical paravertebral nerve block, brachial plexus nerve block, elbow nerve block, wrist nerve block, subarachnoid nerve block, celiac plexus nerve block, deep peroneal nerve block, saphenous nerve block, sural nerve block, popliteal nerve block, tibial nerve block, femoral nerve block, sciatic nerve block, interscalene plexus nerve block, supraclavicular plexus nerve block, axillary plexus nerve block, median nerve block, radial nerve block, ulnar nerve block, brachial plexus nerve block, cervical sympathetic nerve block, stellate ganglia nerve block, and retro bulbar nerve block. Any pathway where a nerve travels has a plane of tissue-separating structures (an interfascial plane), which is a possible route of administration in accordance with the present invention.

A pharmaceutical composition of the present invention may be delivered into a nerve that is to be blocked. In the context of the present invention, a nerve that is to be blocked includes a single nerve bundle or preferably a group of nerve bundles, the latter which may be referred to as either a nerve truck or a nerve ganglion.

Preferably, administration of pharmaceutical composition is in proximity to a nerve that is to be blocked. In order to be "in proximity" to a nerve that is to be blocked, a pharmaceutical composition should be delivered as close as possible to the nerve without being delivered into the nerve itself.

When ultrasound is used for localizing a nerve, being in proximity to a nerve means that a needle used to deliver a pharmaceutical composition of the present invention is as close as possible to the nerve without penetrating the nerve. Being in proximity to a nerve may be visualized for example where a needle used to deliver a pharmaceutical composition is as close as possible but not penetrating a nerve. In one embodiment, this includes where a needle is touching but not penetrating a nerve to be blocked.

Administration may be conducted by a skilled practitioner who conducts a nerve block by administering a pharmaceutical composition of the present invention in proximity to anatomical landmarks such as for example bone, muscle or nerve. Fluoroscopy or computed tomography ("CT" or "CAT") may be used to guide a needle to a location in proximity to a nerve that is to be blocked. Electrical nerve stimulation may also be used to locate a nerve in order to deliver a pharmaceutical composition of the invention in proximity to the nerve. In a preferred embodiment, administration in proximity to a nerve may be guided by ultrasound.

Pharmaceutical compositions of the present invention may also be used in combination with ultrasound therapy, heat or ice therapy.

Pharmaceutical compositions according to the present invention may also be administered as a nerve block to a central (neuraxial) nerve, such as for example by way of a spinal block or an epidural block. In such cases, the dosage of ester anesthetic is likely to be significantly reduced to account for administration into a highly avascular plane.

Administration of pharmaceutical compositions of the present invention may result in sensory (i.e., pain) reduction or elimination with or without paralysis of muscles. In a preferred embodiment, pharmaceutical compositions of the present invention result in sensory reduction or elimination without muscle paralysis.

Administration of a mixture or composition of the present invention may continue for as long as desired to treat a subject. Duration of administration to a subject may be determined for example by a clinician. In determining over what period of time a mixture or composition of the present invention will be administered, a clinician may consider factors such as for example a subject's response to treatment, emergence of side effects, development of tolerance and the like.

In the context of the present invention, a subject to be treated may include any subject in need of treatment or prevention of pain. By way of non-limiting example, a subject may be a mammal, bird or reptile. Exemplary mammals include primates, felines, canines, equines, bovines, lagomorphs, artiodactyls, and marsupials. In a preferred embodiment, a subject is a human.

A subject in need of treatment or prevention may include any subject who is experiencing or is expected to experience any type of pain, including acute or chronic pain. Pain that is treated or prevented may be neuropathic, which is caused for example by damage or disease that affects the nervous system. Pain that is treated or prevented may be nociceptive pain, such as for example that caused by tissue damage or injury, including for example pain associated with surgery, broken bones, lacerations or abrasions. Pain may also be mixed such that it includes both neuropathic and nociceptive pain.

In an embodiment, pain that is treated or prevented is pain associated with any invasive medical or dental procedure, such as a surgery. Pain associated with an invasive medical or dental procedure may include treatment or elimination of pain during the procedure, after the procedure, or both during and after the procedure. By way of non-limiting example, pain that is treated or prevented may include pain associated with excision, resection, laparotomy, laparoscopy, ostomy, ligation, graft, transplant, debridement, or fistula, hernia or prolapse repair. Pain that is treated or prevented may include without limitation pain associated with joint replacement, back or neck surgery, hip surgery, limb surgery, or abdominal surgery. Pain that is treated or prevented using the pharmaceutical compositions and methods of the present invention may include for example, gall bladder surgery, open heart surgery, appendectomy, hysterectomy, mastectomy, tumor removal, plastic surgery, bariatric surgery, oral surgery or labor and delivery.

In another embodiment, pain that is treated or prevented is pain associated with recovery from an injury. Pain associated with recovery from an injury may include for example, pain caused by a burn, laceration, abrasion, bruise, pinched nerve, whiplash, fracture, dislocation, peripheral limb pain, phantom limb pain, intra-abdominal pain, or any combination thereof.

In a further embodiment, pain that is treated or prevented is chronic pain associated with chronic pain syndrome (CPS). Chronic pain syndrome is chronic pain that has been present for at least about 3-6 months.

By the methods of the present invention, pain in a subject may be reduced or eliminated as compared with pain before treatment of the subject. Alternatively or additionally, pain in a subject may be reduced as compared with pain in a similar subject who did not undergo a method of treatment in accordance with the present invention. A similar subject is one who for example undergoes the same surgery or medical procedure or sustains a similar injury, any of which is known by a skilled artisan to result in pain.

In a preferred embodiment, administration results in a perception of numbness by a subject. Numbness may be complete or partial. In a preferred embodiment, numbness is complete. Complete numbness means that a patient does not respond to or perceive painful stimuli such as for example pin pricks or incision with a scalpel.

Reduction of pain includes a reduction in pain by any amount and may be measured by any means conventionally used by the skilled artisan to evaluate pain in a subject. Elimination of pain in a subject means that no pain is detected in a subject as measured by conventional means or the subject reports no pain. Reduction of pain may be found where a subject perceives partial or complete numbness. Elimination of pain is observed where a subject perceives numbness, no pain, or both.

Human subjects may describe a reduction or elimination of pain subjectively, for example by describing pain from a surgery or traumatic injury known to cause severe pain as "mild", "moderate", "better", "much better", "manageable", "more manageable", "tolerable", or "more tolerable."

Effective treatment of pain in a subject may include reduction of any type of pain, including for example decreased burning, pricking, tingling, aching, throbbing, stinging, soreness or any combination thereof in the subject.

Reduction of pain may be measured by any conventional means known to the skilled artisan. For example, in some rodents, a tail flick study may be used to assess pain before and after administration of a pharmaceutical composition of the invention. For a human subject, self-reporting, for example using a graded scale of (0) no pain to (10) maximum pain, may be used to identify decreased pain. Alternatively, functional magnetic resonance imaging (fMRI) may be used in a subject to identify decreased pain following administration of a pharmaceutical composition of the present invention. A reduction in pain may also be ascertained by a skilled practitioner who finds that administration of additional pain-relieving medication is not required after a procedure or injury where additional pain-relieving medication is typically required.

By any method used for measurement, upon administration of a pharmaceutical composition of the present invention, pain may be reduced by about 10%, about 20%, about 30%, about 40%, about 50%, about 60%, about 70%, about 80%, or about 90% as compared with the pain of a subject who has undergone a similar procedure or trauma. Pain may also be eliminated, which represents numbness, no perception of pain, or both.

In accordance with the present invention, a single administration of a pharmaceutical composition may result in a reduction or elimination of pain in a subject for about 6 hours, about 8 hours, about 10 hours, about 12 hours, about 14 hours, about 16 hours, about 20 hours, about 24 hours, or about 36 hours. In other preferred embodiments, reduction or elimination of pain in a subject may last for about 2 days, about 3 days, about 4 days, about 5 days, about 6 days, or about 7 days. In further embodiments, reduction or elimination of pain in a subject may last for about 2 weeks, for about a month, or for about 6 months.

Pharmaceutical compositions of the present invention and methods of treatment or prevention using such pharmaceutical compositions surprisingly result in pain treatment or prevention for durations that exceed durations expected by a skilled artisan based on the drug, route and dosage administered. Increased duration of pain treatment or prevention using pharmaceutical compositions and methods of the present invention may be at least about 1.5× as long, at least about 2× as long, at least about 3× as long, at least about 4× as long, or at least about 5× as long as expected by a skilled artisan. For example, a pharmaceutical composition of the present invention administered as a nerve block to an interfascial plane or a peri-neural location may have a duration at least about 1.5× as long, at least about 2× as long, at least about 3× as long, at least about 4× as long, at least about 5× as long as administration of an ester anesthetic or an amide anesthetic alone as a nerve block to an interfascial plane or a peri-neural location.

Depending on the source and severity of pain, administration of a pharmaceutical composition of the present invention may be conducted as frequently as desired according to the judgment of a skilled artisan in order to reduce or eliminate a subject's pain. For example, by way of non-limiting example, a nerve block may be conducted about once every 48 hours, once a week, once every two weeks, once a month, once every two months or twice per year. It is also contemplated that the mixtures and compositions of the present invention may be administered in an extended release formulation, such as a formulation that is suitable for dosing, for example without limitation, once a week, once every two weeks, or once a month.

In addition to having an unexpectedly long duration in the treatment or prevention of pain, pharmaceutical compositions of the present invention and methods of treatment or prevention using such pharmaceutical compositions also surprisingly result in pain treatment or prevention without various side effects found with use of other pharmaceutical compositions and methods of treatment. For example, by using the pharmaceutical compositions and methods of the present invention, a decreased need for narcotic drug administration, which is both surprising and beneficial, has been found.

Decreased sedation has also been found as well as increased respiratory output, oxygen saturation or both as compared with prior compositions and methods for treatment or prevention of pain using narcotics. A reduction of side effects, including for example nausea, vomiting, constipation, and addiction, has also been found by using the pharmaceutical compositions and methods of the present invention in lieu of previously known compositions and methods for treatment and prevention of pain, such as for example narcotics.

The present pharmaceutical compositions and methods of use also provide unexpectedly high levels of patient satisfaction and decrease interventions required by health care personnel for pain management. Hospital-wide reduction in IV-narcotics for pain management has been achieved by use of pharmaceutical compositions and methods of the present invention. Better overall hospital pain scores surprisingly have also been recorded upon use of the pharmaceutical compositions and methods of the present invention. Earlier discharge of subjects from the hospital and better insurance reimbursement have been observed as further surprising and beneficial results of using the pharmaceutical compositions and methods of the present invention.

EXAMPLES

While the present invention has been described by reference to various embodiments, the present invention is not in any way limited to the specifically disclosed embodiments. The present description is not intended to limit the present invention; to the contrary, various modifications will be apparent to those skilled in the art by reference to the description of the present invention. Such modifications, alternatives, and equivalents fall within the spirit and scope of the present invention.

Example 1—Femoral Nerve Blocks

Shown below is data that was gathered from patients treated with a femoral nerve block to relieve pain associated with trauma or surgery (including post-surgical pain). Each bar in the graph corresponded to at least 20 patients.

In order to prepare tetracaine for administration, 40 mg of tetracaine (4 mL), provided as tetracaine hydrochloride injection, 1% (Akorn,® Lake Forest, Ill.), was dissolved in a carrier of solution of 30 mL of ropivacaine HCl (Naropin®, Lake Zurich, Ill.). In other blocks for other patients (data not shown), tetracaine was also used in dosages ranging from 5-100 mg.

The concentration of ropivacaine in the carrier solution was as indicated below in the Femoral Nerve chart. In other blocks for other patients (data not shown), bupivacaine was also used as a carrier in a 0.25% solution.

Physostigmine, provided as physostigmine salicylate injection, 1%, (Akorn®, Lake Forest, Ill.) was also added at a dosage of 500 µg as indicated in the chart below. In other blocks for other patients (data not shown), peridostigmine was also used at a dosage of 1000 µg.

Drugs were administered in a conventional fashion as a femoral nerve block using ultrasound to locate the femoral nerve.

Control patients ("Fem Plane") received 30 mL of a carrier solution alone, where the solution contained 0.2% ropivacaine, 0.35% ropivacaine, or 0.5% ropivacaine as indicated. Blocks lasted in an expected range of 4-24 hours for these control patients, in accordance with applicable literature.

By reference to the Femoral Nerve chart (FIG. 1), "Fern T+P500" patients received 40 mg tetracaine plus 500 µg physostigmine, dissolved in a carrier solution containing 30 mL of 0.2% ropivacaine, 0.35% ropivacaine, or 0.5% ropivacaine as indicated.

As noted above, when a ropivacaine solution alone was administered in a conventional manner via a femoral nerve block, an expected duration of effect (i.e., 4-8 hours) was achieved. However, when tetracaine and physostigmine were added, a surprising and unexpected effect was found. The block duration as measured by patient satisfaction and failure to request additional pain control measures was surprising and unexpected.

Surprisingly, the duration of effect for tetracaine and physostigmine in a solution of 0.2% ropivacaine was about 18 hours. This far exceeds the about 4 hour duration of pain control seen with a 0.2% solution of ropivacaine alone.

Moreover, tetracaine and physostigmine together with either 0.35%, 0.4% (data not shown), or 0.5% ropivacaine resulted in pain control having a significantly longer than expected duration than observed for ropivacaine alone. In particular, the duration of pain control increased to almost 30 hours or 50 hours with 0.35% or 0.5% ropivacaine, respectively.

Example 2—Paravertebral Block

Figure 2:
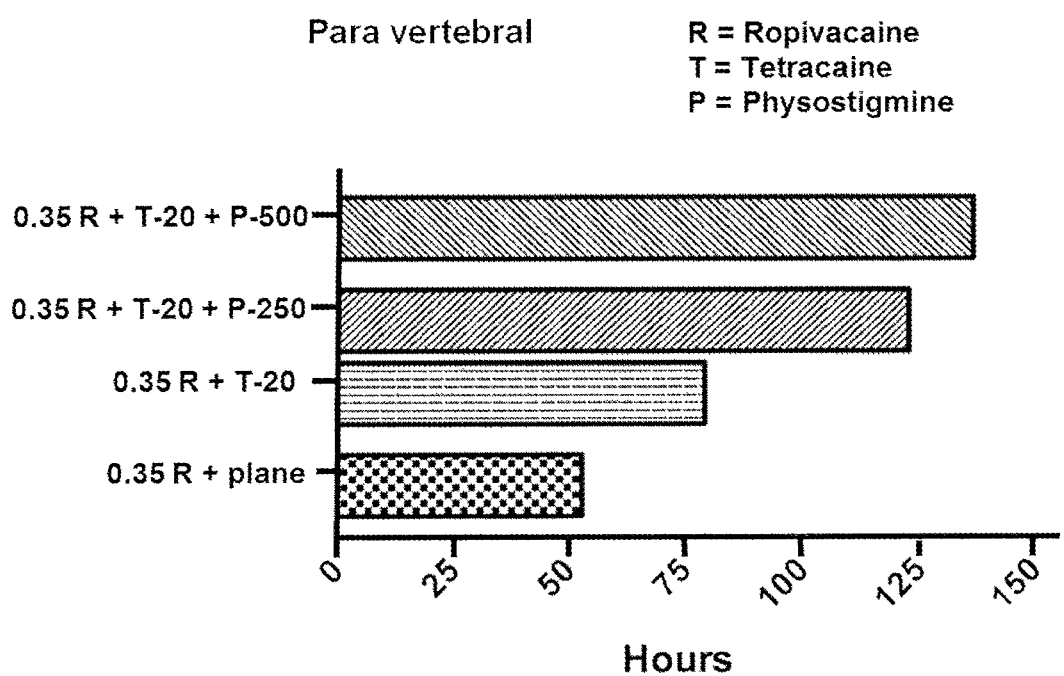
FIG. 2 shows paravertebral block duration in patients receiving 0.35% ropivacaine alone or 0.35% ropivacaine with 20 mg tetracaine, or 0.35% ropivacaine with 20 mg tetracaine and 250 μg or 500 μg physostigmine.

Shown in FIG. 2 is data that was gathered from patients treated with a paravertebral block to relieve pain. In accordance with all bars in the graph 0.35% ropivacaine was administered to all patients as shown in the below Paravertebral chart. The bar corresponding to 0.35% ropivacaine alone reflected data gathered from greater than 20 patients. For all patients other than 0.35% ropivacaine alone, 20 mg of tetracaine was also added. Where 0.35% ropivacaine was combined with 20 mg tetracaine, data was gathered from 4 patients. Where physostigmine was also added, at either 250 mg or 500 mg as indicated in the chart below, data reflects that gathered from at least 10 patients each.

As in the femoral example above, for the paravertebral blocks, tetracaine was provided as tetracaine hydrochloride injection, 1% (Akorn,® Lake Forest, Ill.) and was dissolved in a carrier of solution of 30 mL of ropivacaine HCl (Naropin®, Lake Zurich, Ill.). Physostigmine, when added, was provided as physostigmine salicylate injection, 1%, (Akorn®, Lake Forest, Ill.) and was added at the indicated dosages of 250 µg or 500 µg.

Drugs were administered in a conventional fashion as a paravertebral nerve block using ultrasound to locate the paravertebral nerve.

By reference to the Paravertebral chart in FIG. 2, it can be observed that addition of 20 mg of tetracaine to a 0.35% ropivacaine carrier solution significantly increased the duration of pain control as compared with ropivacaine alone. Moreover, when physostigmine was added at either 250 µg or 500 µg, a further significant increase in pain control was achieved. These results provided a surprising and beneficial achievement.

Example 3—Scalene Block

Figure 3:
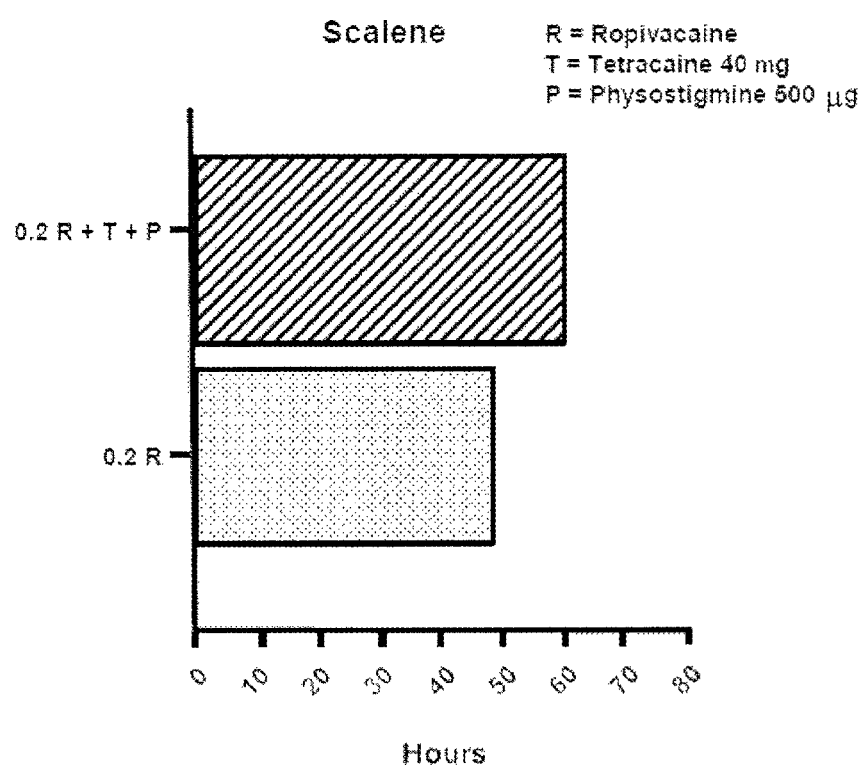
FIG. 3 shows scalene block duration in patients receiving 0.2% ropivacaine alone or 0.2% ropivacaine with 40 mg tetracaine and 500 μg physostigmine.

Shown in FIG. 3 is data that was gathered from patients treated with a scalene block to relieve pain. Each bar in the graph corresponded to at least 8 patients.

Forty (40) mg of tetracaine (4 mL), provided as tetracaine hydrochloride injection, 1% (Akorn,® Lake Forest, Ill.), was dissolved in a carrier solution of 30 mL of 0.2% ropivacaine HCl (Naropin®, Lake Zurich, Ill.). Physostigmine, provided as physostigmine salicylate injection, 1%, (Akorn®, Lake Forest, Ill.) was added at a dosage of 500 µg. Other patients ("controls") received 30 mL of a carrier solution alone, where the solution contained 0.2% ropivacaine.

Drugs were administered in a conventional fashion as a scalene block using ultrasound to locate the injection site.

While blocks containing 0.2% ropivacaine alone lasted about 48 hours, from the Scalene chart in FIG. 3, it can be observed that scalene blocks containing 40 mg of tetracaine and 500 µg of physostigmine in addition to 0.2% ropivacaine lasted more than 60 hours.

Example 4

Numerous other blocks were conducted at varying sites using varying concentrations of ropivacaine carrier from 0.1% to 0.5%, tetracaine from 10 mg to 100 mg, and physostigmine from 10 µg to 2000 µg. Based on these numerous blocks, a surprising and unexpected prolongation of block time was observed when tetracaine was added to blocks. A further surprising and unexpected prolongation of block time was observed when both tetracaine and physostigmine were added to blocks.

Example 5

Tolerability of physostigmine was tested up to 2000 µg in various types of block. More than 300 patients were administered varying concentrations of physostigmine. Of these, only 5 patients have showed any adverse reaction, with four of those adverse reactions resulting from a dosage of 2000 µg.

More than 50 patients were administered 250 µg of physostigmine. None of these patients showed an adverse reaction.

More than 200 patients were administered 500 µg of physostigmine. Of these patients, only one patient showed a potential adverse reaction, i.e., nausea, which was successfully managed so that the patient had no long term effects.

More than 10 patients were administered 750 µg of physostigmine. None of these patients showed an adverse reaction.

Eight patients were administered 2000 μg of physostigmine. Of these patients, four patients (all with paravertebral blocks) had adverse effects, including nausea, vomiting, and bradycardia, all of which were medically managed to a successful outcome.

What is claimed:

1. A pharmaceutical composition comprising about 10 mg to about 100 mg tetracaine or pharmaceutically acceptable salt thereof and about 100 μg to about 1000 μg physostigmine or pharmaceutically acceptable salt thereof.

2. The pharmaceutical composition according to claim 1, further comprising ropivacaine or pharmaceutically acceptable salt thereof as a carrier.

3. The pharmaceutical composition according to claim 2, wherein the ropivacaine or pharmaceutically acceptable salt thereof is at a concentration of about 0.1% to about 0.5%.

4. A pharmaceutical composition comprising about 10 mg to about 100 mg tetracaine or pharmaceutically acceptable salt thereof, about 100 μg to about 1000 μg physostigmine or pharmaceutically acceptable salt thereof, and about 0.1% to about 0.5% ropivacaine or pharmaceutically acceptable salt thereof.

* * * * *